United States Patent [19]

Petre

[11] 4,444,198

[45] Apr. 24, 1984

[54] CIRCULATORY MONITORING SYSTEM AND METHOD

[76] Inventor: John H. Petre, 3253 Bradford Rd., Cleveland Heights, Ohio 44118

[21] Appl. No.: 332,737

[22] Filed: Dec. 21, 1981

[51] Int. Cl.³ .............................................. A61B 5/02
[52] U.S. Cl. ...................................... 128/673; 604/30
[58] Field of Search ............................... 128/673–675; 604/30–31, 34, 118, 127, 246, 250, 269

[56] References Cited

U.S. PATENT DOCUMENTS

| | | | |
|---|---|---|---|
| 3,157,201 | 11/1964 | Littman | 604/32 |
| 3,565,056 | 2/1971 | Statham | 128/675 X |
| 3,675,891 | 7/1972 | Reynolds et al. | 128/673 X |
| 3,713,341 | 1/1973 | Madsen et al. | 128/675 X |
| 4,291,702 | 9/1981 | Cole et al. | 128/675 |
| 4,300,571 | 11/1981 | Waldbillig | 128/673 |
| 4,381,591 | 5/1983 | Barger et al. | 604/30 |

*Primary Examiner*—Kyle L. Howell
*Assistant Examiner*—Francis J. Jaworski
*Attorney, Agent, or Firm*—Maky, Renner, Otto & Boisselle

[57] ABSTRACT

A sterile intra-circulatory monitoring system utilizing an indwelling catheter with fluid under pressure being forced through a fluid line to the catheter. The system includes a normally stagnant pressure chamber to which a transducer is connected. The contents of the chamber are periodically flushed back into the fluid line by utilizing a flush valve and a venturi unit. The venturi unit may be an integral part of the flush valve or separate component. With the present invention a closed loop system is utilized which does not compromise the sterility of the system or the environment.

54 Claims, 6 Drawing Figures

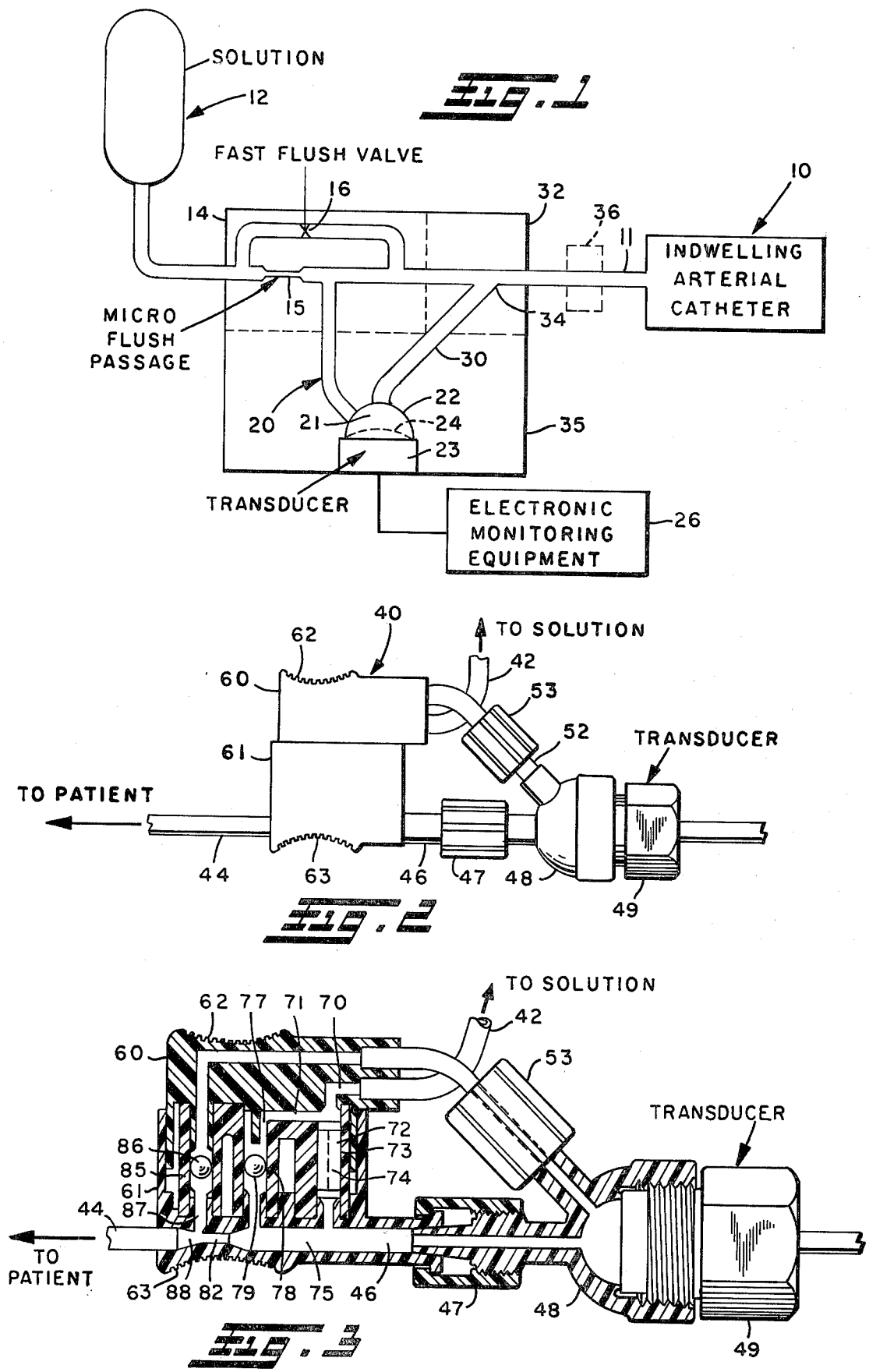

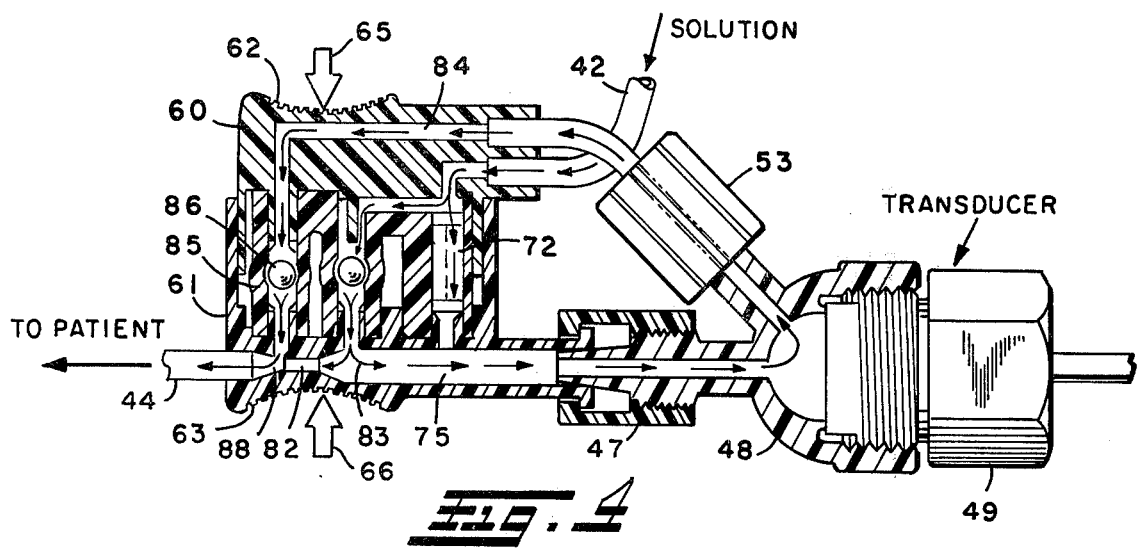
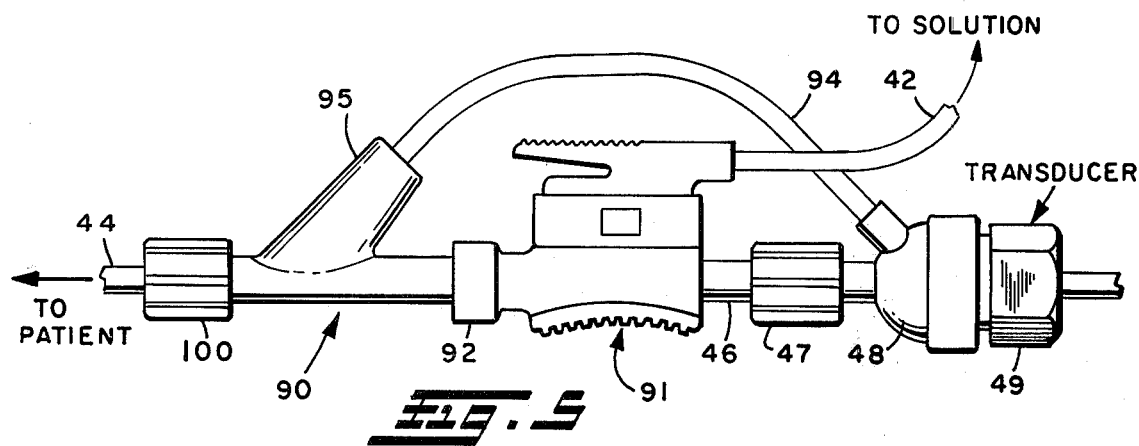
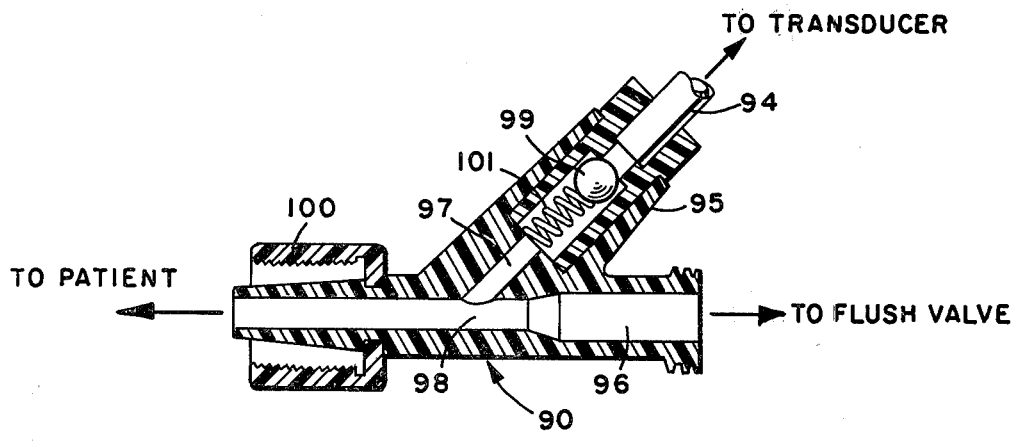

ized to approximately 300 mm Hg. Positioned
CIRCULATORY MONITORING SYSTEM AND METHOD

BACKGROUND OF THE INVENTION

This invention relates generally as indicated to an intra-circulatory monitoring system and method and a flush system therefor.

In the care of critically ill patients, a system known as intra-arterial monitoring has been developed for gathering accurate and reliable data for use in the diagnostic treatment and care of such patients. This technique is used for example, for obtaining patient blood pressure on a continuous basis. Such technique involves direct and continuous measurement of the blood pressure and is more accurate than indirect measurements obtained with an occlusive cuff. Cuff pressure values can be distorted by a variety of factors such as incorrectly applied cuffs or ill-fitting cuffs, or by pressures so low that sounds are lost.

Such intra-arterial monitoring systems involve the use of an indwelling catheter, a pressure transducer, a tubing and coupling system, and an electronic device for calculating and displaying patient blood pressure values on a continuous basis. This technique is now routinely used in operating rooms, intensive care units, and other areas of a hospital devoted to critical patient care and may be employed substantially anywhere in the circulatory system.

A primary component of the system is the monitoring device which, in the case of blood pressure observation, is a pressure transducer. This device is employed as a converter to change pressure from the blood within the artery to a proportional electronic signal. The pressure wave forms sensed by the transducer are displayed as analog signals on a cathode ray tube for visual study. Digital values such as the peak or systolic pressure and trough or diastolic pressure are calculated and displayed directly in digital form. This information is normally updated on a continuous basis to indicate or approximate real time values.

Such systems may also be used to take frequent blood specimens eliminating the need for frequent venipunctures. The system may also be used to facilitate the control or application of fluids within the blood such as heparin or protamine used before, during and following critical surgical procedures such as open heart surgery.

While the system has become commonplace in the treatment of critically ill patients, it is nonetheless of great importance that the display data be accurate, dependable and repeatable. As with any complex system, there are disadvantages which may develop which may compromise the system if they are not recognized and controlled. Some of the more frequent disadvantages in such systems are the contamination of the tubing system and the clinical use of any inaccurate data resulting from a system malfunction such as a transducer gain mismatch, improper zeroing, calibration, etc. Furthermore, as with other sensitive monitoring systems, signal damping and system noise are preferably minimized.

In the case of contamination, foreign substances introduced into the fluid system may result in inaccurate data. Typical examples are air bubbles and blood clots present in the fluid stream. A common form of such contamination which may result in distortion of the data obtained is the formation of air bubbles in the usually dome-shape pressure chamber to which the transducer is connected. These air bubbles or pockets generally accumulate from the atomizing effects of a solution under pressure passing through small orifices or may be remnants of poor set up and the initial flushing of the monitoring system.

Reference may be had to an article entitled "Intra-arterial Monitoring, Rescinding the Risks" of JoAnn Lamb, which appeared in the November, 1977 issue of Nursing '77 for a general description of such monitoring systems and some of the problems involved. A typical intra-arterial monitoring system comprises an indwelling arterial catheter which is inserted in an artery of the patient. The catheter is connected through a dynamic fluid line to a source of heparin enriched saline solution pressurized to approximately 300 mm Hg. Positioned within such line is a flush valve which includes a micropassage or restricted orifice through which solution passes into the catheter. The flush valve also includes a bypass passage so that the micropassage may be bypassed when desired. The system usually includes a static or dead end line positioned downstream of the micropassage which leads to a domed pressure chamber to which the transducer is connected. The transducer is, of course, connected to the electronic monitoring equipment. The transducer dome is transparent and is normally provided with a stopcock for manual venting.

The pressure of the saline solution is normally above the arterial pressure and assures a flow of the solution into the artery when needed. Heparin is normally employed to dissolve and discourage blood clots which might accumulate anyplace in the monitoring system, particularly in the indwelling catheter site.

The flush valve contains a metering orifice or passage that permits a constant controlled microflow of the heparin solution into the artery thus keeping the system free of clots and enhancing the accuracy of the fluid pressure generated electronic signals. The primary fluid flow line of the pressurized solution to the artery is intended to be a dynamic flowing line.

It is standard technique to clear this primary flow line occasionally of accumulated air or clots not handled by the microflow. It is also routine practice to withdraw arterial blood specimens through this line. Such withdrawal results in blood being aspirated up into the monitoring line. It therefore becomes necessary periodically to fast flush the blood, clots and air out of the primary dynamic line implementing the more rapid flow of the flush solution for a short period of time. This is normally accomplished by a manual actuation of the flush valve which momentarily bypasses the micropassage within the valve and such action then produces a more rapid flow condition in the primary line from the pressurized solution to the indwelling catheter.

Conventionally, the static line or passage connects from the flush valve downstream of the micropassage to a dome chamber which contains an isolation membrane to confine the fluid. The transducer and dome are assembled such that the membrane is in intimate contact with the transducer diaphragm thus sensing pressure on the membrane. The membrane permits the changing of transducers which are normally quite expensive and not disposable without compromising the sterility of the monitoring system. Accordingly, the static fluid branch to the transducer chamber and membrane is a stagnant line under normal monitoring and fast flush procedures.

In such systems, the dome or chamber is usually provided with a stopcock which may be opened to purge air or unwanted fluids from the dome to air or ambient atmosphere. The venting of air and/or fluids from the transducer chamber or dome by the stopcock method is at best a messy situation. Fluids within the dome can and do run over the transducer and dome making removal and separation difficult. Moreover, the patient may be draped for surgery and such venting may contaminate the sterile environment. Opening of the stopcock may require the use of both hands and must be done initially when the system is first set up and flushed, and then every time air or blood accumulates within the chamber.

SUMMARY OF THE INVENTION

The present intra-circulatory monitoring system and method utilizes a closed loop system associated with the catheter side of a flush valve and extending to a monitoring device. The loop may at all times remain sealed, it not being necessary to open the loop in order to purge air or fluids from the chamber of the monitoring device or the monitoring system at initial set-up or at anytime during its use. Moreover, the entire system including a transducer dome or a chamber is automatically purged of air or other undesirable fluids each time the system is fast flushed.

Through the employment of the closed loop system, the present utilization of a manually operated stopcock to purge bubbles from the dome or pressure chamber at set up or thereafter may be eliminated. The purging or flushing of the chamber becomes a simple set up for continued periodic operation for nursing personnel. Moreover, the hazards and mess of uncontrolled heparin or other fluids contaminating transducers or other monitoring devices, drapes or other sensitive environment is eliminated. Also, it is not then necessary for nursing personnel to closely monitor the transducer dome or chamber of the monitoring device for the presence of air bubbles or other fluid contaminants since periodic fast flushing will automatically purge or flush the chamber insuring reliable readings. Thus, the close visual observation of the dome or chamber coupled with the normal two-hand requirement for manipulation of the stopcock which tends to divert the effort and attention of skilled nursing personnel from other more vital tasks is avoided.

The closed loop may be arranged in the system such that communication between the ends of the loop and the catheter creates a pressure differential between the ends of the loop at least during fast flush operation. To this result, a venturi has been employed in association with one of the loop ends. Thus, fast flush flow may be employed to induce a current in the monitoring loop to also flush the loop and the chamber of the monitoring device.

The system may include a valve means by which flow through the closed loop may be controlled to occur only during flush flow of the monitoring system. Such a valve can reduce system noise by eliminating flow to the monitoring device during normal operation. Such valving can also be employed to reduce the effective volume of the system to reduce correspondingly the attenuation of the monitored signal.

It is accordingly a principal object of the present invention to provide an intra-circulatory monitoring system which includes a closed loop through the transducer pressure chamber which may be flushed without compromising the accuracy of the system.

Another principal object is the provision of such system wherein the static line and chamber through which the blood pressure is monitored may be periodically flushed without comprising the sterility of the system.

Another important object is the provision of such system which includes means to periodically purge the transducer chamber of unwanted fluids or small quantities of air back into the dynamic fluid line.

Still another important object is the provision of such system which indicates both a dynamic line and a static line leading to the transducer pressure chamber with means providing closed loop periodic flushing of the pressure chamber back to the dynamic line.

Yet another important object is the provision of such system which comprises the steps of providing a normally static chamber through which blood pressures may be continually monitored, but which may be periodically flushed.

Still another object is the provision of such system whereby such flushing may be accomplished by conventional flush valves in the system.

A further object is the provision of such system which incorporates a venturi unit.

Also an object is the provision of such system wherein the venturi unit is operable only in conjunction with a flush valve.

A still further object is the provision of such system wherein the venturi unit may be an integral part of the flush valve.

Yet another object is the provision of such unit wherein the venturi unit may be a separate component.

Still another object is the provision of such system which includes a closed loop system that does not compromise the sterility of the system or its environment.

Other objects and advantages of the present invention will become apparent as the following description proceeds.

To the accomplishment of the foregoing and related ends, the invention then comprises the features hereinafter fully described and particularly pointed out in the claims, the following description and the annexed drawings setting forth in detail certain illustrative embodiments of the invention, these being indicative, however, of but a few of the various ways in which the principles of the invention may be employed. Additional components providing further functions to the system such as stopcocks and the like may be incorporated where advantageous.

BRIEF DESCRIPTION OF THE DRAWING

In said annexed drawings:

FIG. 1 is a semi-schematic illustration of one form of the present invention wherein the invention includes the closed loop, transducer dome and venturi unit as an integral part of the flush valve;

FIG. 2 is an elevation with components broken away wherein the venturi system for the transducer chamber is incorporated in a flush valve;

FIG. 3 is a somewhat enlarged section in the plane of the page of the system seen in FIG. 2;

FIG. 4 is a view similar to FIG. 3 showing the condition of the parts in the flush condition;

FIG. 5 is a view similar to FIG. 2, but illustrating the venturi unit as a separate component from the flush valve; and FIG. 6 is an enlarged section in the plane of the page of the unit seen in FIG. 5.

DETAILED DESCRIPTION OF THE PREFERRED EMBODIMENTS

Referring first to FIG. 1, there is illustrated an intra-arterial monitoring system which incorporates the improvements and method of the present invention. The system illustrated comprises an indwelling arterial catheter indicated at 10 which may be inserted into an artery of the patient. The catheter is connected through a primary dynamic fluid passage 11 to the source of solution under pressure as indicated at 12. Positioned within the dynamic passage 11 between the solution source 12 and the indwelling arterial catheter 10 is a fast flush valve indicated schematically at 14. The flush valve 14 includes a micropassage 15 and a bypass valve 16 which may be manually opened. When the valve 16 is opened, usually by finger squeezing a flexible chamber, the solution from the pressurized source 12 bypasses the micro flush passage 15 flushing the dynamic line 11. The solution at the source 12 is normally a heparin enriched saline solution which is pressurized to about 300 mm Hg. This pressure is normally above the arterial pressure and assures a flow of the solution into the artery when needed.

In conventional systems, the flush valve is usually employed to clear the dynamic line periodically of accumulated air or clots which are not handled by the microflow passage 15. It is also routine practice to withdraw arterial blood samples through the primary dynamic line 11 and such withdrawal may result in blood backing up into the monitoring line making it necessary to fast flush the blood, clots and air out of the line by a more rapid flow of the heparin solution for a short period of time. This is normally accomplished by activating the manually operated flush valve which momentarily bypasses the micro flush passage. This action then produces a more rapid flow condition than the primary line from the pressurized solution to the indwelling catheter.

Conventionally, such systems are provided with a branch or static line downstream of the micro flush passage 15 as indicated at 20 which leads to a chamber 21 normally in the form of a dome 22 to which the transducer 23 is connected. The dome 22 contains an isolation membrane indicated generally at 24 which is in intimate contact with the transducer diaphragm thus sensing pressure on the membrane. This construction permits the changing of transducers which are usually expensive and not disposable without compromising the sterility of the fluid system. The pressue waveforms sensed by the transducer 23 are displayed as analog signals through the electronic monitoring equipment indicated at 26, as analog signals on a cathode ray tube for visual study. Digital values such as the peak or systolic pressure and trough or diastolic pressure may be calculated and displayed directly in visual form.

Normally, the dome would be provided with a stopcock valve which would require to be opened manually to vent any bubbles of unwanted air or fluids which might occur therein. As indicated, this would require immediate attention necessitating two-hand manipulation by an attendant nurse.

However, with the present invention, a connection indicated generally at 30 is provided from the dome or chamber 22 back to the primary line 11. This connection may lead from the dome either at its top as indicated in FIG. 1, or from the top side of the dome as indicated in subsequent figures back to the primary line 11 through a venturi unit seen at 32. The unit 32 includes primarily a venturi indicated generally at 34.

In the embodiment illustrated in FIG. 1, the passages 20 and 30 as well as the chamber 21 forming the closed loop system are incorporated in body 35 which may be secured to or integral with the flush valve 14 and venturi unit body 32. With the invention the dome need not be visible and the construction illustrated avoids assembly and fitting connection otherwise performed at set up. It can now be seen that because of the closed loop system provided by the normally static passage 20 and the chamber 21 through the connection 30, that when the fast flush valve is operated, chamber 21 will also be flushed of air or other contaminants insuring the proper functioning of the transducer. As indicated in the primary or dynamic line 11, downstream of the venturi 34, there may be provided an optional filter indicated at 36 for venting gases.

The present invention may take the form as shown in FIG. 2 wherein the flush valve indicated generally at 40 may include as part of the primary or dynamic fluid line an inlet line indicated at 42 connected to the pressurized solution. The primary line also includes an outlet line 44 connected to an indwelling catheter in the patient. From such valve there is extended a static line 46 connected through quick connect coupling 47 to dome or pressure chamber 48. The dome or pressure chamber 48 provides a pressure chamber in intimate contact with a fluid diaphragm which is in turn in intimate contact with the transducer 49. As indicated, the dome or pressure chamber is also provided with a passage 52 which leads through the quick connect coupling 53 back to the top of the flush valve 40. The flush valve may include two relatively movable portions indicated by the upper portion 60 and the lower protion 61 which are movable toward each other by placing opposed fingers on the two opposed gripping portions 62 and 63, respectively. This actuates the valve as seen more clearly by the arrows 65 and 66 as seen in FIG. 4. The flush valve may be a modification of a flush valve of the type manufactured and sold by Bentley Laboratories Inc., of Irvine, Calif.

As seen more clearly in FIGS. 3 and 4, the modified flush valve may include the upper portion 60 which telescopes into the lower or body portion 61 with the upper portion including the primary line connection 42 to the solution. Such solution enters the upper portion through the passage 70 which branches horizontally as indicated at 71. The passage 70 is in communication with a capillary unit 72 fitting snugly in vertical passage 73, such capillary unit including a small vertically oriented microflow passage 74. Solution passing through the microflow passage enters the main passage 75 in the lower or body portion 61.

The branch passage 71 connects with the vertical passage 77 which is formed by a flexible tubular wall 78. When the two parts of the valve are squeezed together as indicated by the arrows in FIG. 4, the flexible wall bows outwardly permitting the fluid to bypass the ball 79 and of course the capillary unit 72. The fluid flows into passage 75.

The passage 75 is provided with a slight restriction seen at 82 causing fluid to flow in both directions as indicated by the arrows 83 in FIG. 4. This then forces the fluid through the normally static line 46 to the dome 48 flushing the contents through line 52 back into the top of the valve. Such fluid then enters the passage 84 in the top of the valve and then downwardly through flexible sleeve 85 around the ball 86. The sleeve 85 is of course flexed to the open or bulging condition seen in FIG. 4 concurrently with the sleeve 78 when pressure is applied to the two parts of the valve as indicated.

The flow past the ball 86 through the sleeve 85 is into passage 87 which communicates with the passage 75 downstream of the restriction 82 communicating directly with the line 44. At such juncture a venturi is provided as seen at 88 to provide a means for reducing pressure at that point in the flow. The venturi 88 creates a pressure differential between the static branch line 46 and the passage 84, the pressure being reduced in passage 84. This facilitates the withdrawal of fluid from the passage 84 and thus from the dome 48.

Referring now to the embodiment of FIG. 5, it will be seen that the venturi unit shown generally at 90 may be in the form of a separate unit which may be quickly connected to the outlet of flush valve 91 as seen at 92. The flush valve 91 may be of the type made and sold by the aforenoted Bentley Laboratories of Irvine, Calif., but without the modifications seen in FIGS. 3 and 4. The valve may be of the type seen in the copending application of Sullivan, Ser. No. 312,856, filed Oct. 16, 1981, entitled "Flow Control Apparatus". Such flush valve would normally include only the capillary 72 and the rapid flush bypass through sleeve 78 and ball 79. Also, it would not include the restriction or a venturi. It should also be noted that any of a wide variety of commercially avilable flush valves may be employed with the system illustrated.

The operation of the system of FIG. 5 is, however, essentially the same, as the earlier described embodiment. Solution normally flows through line 42 under pressure through the capillary of the flush valve 91, through the venturi unit 90 and through line 44 to the patient. The static branch line 46 is connected to the dome 48 of the transducer chamber. The dome is also connected through closed loop line 94 to the angled leg 95 of the venturi unit bypassing the flush valve 91. Thus, in the fast flush condition of the valve 91 solution flows more rapidly through the main passage 96 in the venturi unit, see FIG. 6, drawing solution from the branch line 97 because of the venturi 98 and in turn from the line 94 and the dome or chamber 48. This flow flushes the dome of gas or fluid in response to the fast flush operation of the valve. The venturi unit 90 is connected through the quick connect coupling shown at 100 to the line 44 leading to the indwelling catheter and the patient. A check valve 99 in the venturi unit 90 prevents backflow through line 94 and may be biased by spring 101 to open only when sufficient pressure differential exists between line 94 and the venturi 98, e.g., when fast flush occurs.

It will be appreciated that the units seen in FIGS. 2 through 6 are shown larger than actual size and that the valves illustrated may readily be actuated by finger pressure on the opposed parts.

It can now be seen that there is provided a closed loop system in intra-circulatory monitoring for flushing gases or contaminating liquids from the pressure chamber of the transducer without contaminating the system or the environment and insuring repeatable and reliable readings from the transducer.

I claim:

1. In an arterial monitoring system combination, an indwelling catheter, a source of solution under pressure, a dynamic line connecting the catheter to the source, a chamber between said source and catheter, a normally static line connecting the dynamic line to the chamber, a transducer operative to monitor pressure fluctuations in the chamber, and means to flush said chamber to said dynamic line without compromising the system when said chamber is closed or non-vented to the atmosphere.

2. A system as set forth in claim 1 including a second normally static line leading from said dynamic line to such chamber.

3. A system as set forth in claim 2 including a fast flush valve operative periodically to flush such chamber through said first mentioned and second normally static lines.

4. A system as set forth in claim 2 wherein said fast flush valve when in its fast flush condition is operative momentarily to increase the flow in said dynamic line, and means responsive to such increased flow to assist the flushing of such chamber.

5. A system as set forth in claim 4 wherein said last mentioned means comprises a venturi at the connection of one of said normally static lines and said dynamic line.

6. A system as set forth in claim 5 including valve means in said one of said normally static lines.

7. A system as set forth in claim 6 including means responsive to the fast flush condition of said fast flush valve to open said valve means.

8. A system as set forth in claim 7 including means responsive to the closing of said fast flush valve to close said valve means.

9. A system as set forth in claim 6 wherein said valve means is a check valve.

10. A system as set forth in claim 6 wherein said fast flush valve and said valve means are manually operable concurrently by the same mechanism.

11. A system as set forth in claim 6 wherein said fast flush valve and said valve means are each manually operable.

12. A system as set forth in claim 6 wherein said fast flush valve and said valve means are in the same housing.

13. A system as set forth in claim 12 wherein said housing includes said venturi.

14. A system as set forth in claim 13 wherein said housing includes said chamber.

15. A system for intra-arterial monitoring comprising an indwelling arterial catheter, a source of fluid, and a flush valve and a pressure transducer therebetween, and means responsive to the flush condition of the valve to flush fluid past the transducer without compromising the sterility of the system, said means comprising a closed loop downstream of said flush valve.

16. A system as set forth in claim 15 including a chamber for the transducer in the closed loop.

17. A system as set forth in claim 16 including means responsive to the flush condition of the flush valve to create momentary flow through the loop and thus the chamber.

18. A system as set forth in claim 17 including a venturi operative to assist in creating such momentary flow.

19. A system as set forth in claim 17 including a pump valve operative to assist in creating such momentary flow.

20. A system as set forth in claim 17 including a valve and venturi operative to assist in creating such momentary flow.

21. In an arterial monitoring system, an indwelling catheter, a source of solution under pressure connected by a fluid line to said catheter, a pressure chamber connected to said line, means to mount a transducer on said chamber operative to monitoring pressure fluctuations therein, and means periodically to purge said chamber of unwanted fluids or air back into said line, said means comprising two normally static lines connecting said chamber back to said line.

22. A system as set forth in claim 21 including a fast flush valve, said two normally static lines being connected to said line downstream of said fast flush valve.

23. A system as set forth in claim 22 wherein said two normally static lines are connected at different locations to said line.

24. A system as set forth in claim 23 wherein the connection furthest downstream includes a venturi.

25. A system as set forth in claim 24 wherein the normally static line connected furthest downstream includes a valve.

26. A system as set forth in claim 25 wherein said valve is concurrently operated with said fast flush valve.

27. A system as set forth in claim 26 wherein said valve, venturi, and connections are commonly housed with said fast flush valve.

28. In an arterial monitoring system, an indwelling catheter, a source of solution under pressure connected by a primary fluid line to said catheter, a branch line connected with said primary fluid line, a normally stagnant pressure chamber at one end of said branch line, and means periodically to cause fluid to flow back through said branch line to said primary line.

29. A system as set forth in claim 28 wherein said means comprises a valve and a venturi.

30. A system as set forth in claim 29 wherein said valve is a pump valve.

31. A system as set forth in claim 30 wherein said valve is a fast flush valve.

32. A system as set forth in claim 30 wherein said means also comprises a closed loop through the pressure chamber.

33. A system as set forth in claim 30 wherein said valve and venturi are commonly housed.

34. A system as set forth in claim 33 wherein said valve, venturi and loop are commonly housed.

35. A system as set forth in claim 33 wherein said valve, venturi, loop and chamber are commonly housed.

36. A method of circulatory monitoring comprising the steps of forcing fluid through a fluid line into an indwelling catheter, providing a normally stagnant chamber connected to such line, monitoring pressure fluctuations in such chamber, and periodically flushing such chamber into such fluid line.

37. The method of claim 36 wherein a fast flush valve is positioned to control fluid through such fluid line and said step of periodically flushing such chamber occurs when such fast flush valve is operated.

38. A method as set forth in claim 37 including utilizing a venturi in such fluid line to obtain such flushing.

39. A method as set forth in claim 37 including utilizing a closed loop connecting the fluid line and chamber to flush the chamber.

40. A flush system for a circulatory monitoring system having a fast flush valve, a catheter line in communication with the fast flush valve downstream thereof, a monitoring device and a static line extending between the catheter line and the monitoring device for communication therebetween, comprising a means for reducing pressure in the catheter line downstream of the monitoring device; and
a flush line in communication with the monitoring device and extending to said pressure reducing means.

41. The flush system of claim 40 wherein said pressure reducing means includes a venturi.

42. The flush system of claim 40 further including a chamber at the monitoring device and to which are connected the static line and said flush line, said flush line being located adjacent the top of said chamber.

43. The flush system of claim 40 wherein said flush line includes a check valve preventing flow away from said pressure reducing means.

44. The flush system of claim 43 wherein said check valve includes a bias spring constructed and arranged to bias said valve toward the closed position.

45. The flush system of claim 43 including a valve means located in said flush line for controlling flow therethrough, said valve means being constructed and arranged to open upon actuation of the flush valve.

46. The flush system of claim 45 wherein said valve means is included within the body of said flush valve.

47. A flush system for a circulatory monitoring system having a fast flush valve, a catheter line in communication with the fast flush valve downstream thereof, a monitoring device and a static line extending between the catheter line and the monitoring device for communication therebetween, comprising a venturi downstream of the monitoring device in the catheter line;
a flush line in communication with the monitoring device and extending to said venturi; and
a chamber positioned at the monitoring device to which are connected the static line and said flush line, said flush line being located adjacent the top of said chamber.

48. A flush system for a circulatory monitoring system having a fast flush valve, a catheter line in communication with the fast flush valve downstream thereof, a monitoring device and a static line extending between the catheter line and the monitoring device for communication therebetween, comprising a means for reducing pressure in the catheter line downstream of the monitoring device;
a flush line in communication with the monitoring device and extending to said pressure reducing means, the flush line including valve means for controlling flow therethrough, said valve means being constructed and arranged to open during flush flow through the flush valve.

49. The flush system of claim 48 wherein said pressure reducing means includes a venturi.

50. The flush system of claim 48 wherein said valve means includes a spring biased check valve.

51. The flush system of claim 48 wherein said valve means is incorporated into the housing of said flush valve.

52. The flush system of claim 48 further including a chamber at the monitoring device and to which are connected the static line and said flush line, said flush line being located adjacent the top of said chamber.

53. A circulatory monitoring system, comprising
a fast flush valve;
a catheter line in communication with said fast flush valve downstream thereof;
a monitoring device;

a static line extending between said catheter line and said monitoring device for communication therebetween;

a venturi downstream of said monitoring device in said catheter line; and a flush line in communication with said monitoring device and extending to said venturi.

54. A circulatory monitoring system, comprising a source of fluid;

a catheter line;

a fast flush valve in communication with said source of fluid and said catheter line, said fast flush valve including a capillary passage in communication with said source of fluid and said catheter line for continuous low volume flow therebetween, a fast flush passage also in communication with said source of fluid and said catheter line for fast flush flow therebetween, and a valve device in said fast flush passage for selective control of fast flush flow through said fast flush passage;

a monitoring device;

a static line extending between said catheter line and said monitoring device for communication therebetween;

a venturi downstream of said monitoring device in said catheter line;

a flush line in communication with said monitoring device and extending to said venturi; and a valve means for controlling flow through said flush line, said valve means being constructed and arranged to open during flush flow through said flush valve.

* * * * *